(12) United States Patent
Grundeman et al.

(10) Patent No.: US 10,441,414 B2
(45) Date of Patent: Oct. 15, 2019

(54) METHOD OF MAKING A PROSTHETIC VALVE AND VALVE OBTAINED THEREWITH

(71) Applicant: DSM IP Assets B.V., Heerlen (NL)

(72) Inventors: Paul Frederik Grundeman, Utrecht (NL); Jolanda Kluin, Utrecht (NL); Karlien Kristel Boon-Ceelen, Echt (NL); Thomas König, Utrecht (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/309,003

(22) PCT Filed: May 6, 2015

(86) PCT No.: PCT/EP2015/059984
§ 371 (c)(1),
(2) Date: Nov. 4, 2016

(87) PCT Pub. No.: WO2015/169868
PCT Pub. Date: Nov. 12, 2015

(65) Prior Publication Data
US 2017/0071730 A1    Mar. 16, 2017

(30) Foreign Application Priority Data

May 6, 2014    (EP) ..................... 14167269
May 6, 2014    (EP) ..................... 14167270
(Continued)

(51) Int. Cl.
*A61F 2/82*    (2013.01)
*A61F 2/24*    (2006.01)

(52) U.S. Cl.
CPC .......... *A61F 2/2415* (2013.01); *A61F 2/2412* (2013.01); *A61F 2/2418* (2013.01); *A61F 2220/0075* (2013.01)

(58) Field of Classification Search
CPC ............ A61F 2/2418; A61F 2220/0075; A61F 2/2412; A61F 2/2415; A61F 2220/0008;
(Continued)

(56) References Cited

U.S. PATENT DOCUMENTS 3,526,906 A    9/1970    DeLaszlo
3,859,668 A    1/1975    Anderson
(Continued)

FOREIGN PATENT DOCUMENTS

NL    1008349    8/1999
WO    2000/062714    10/2000
(Continued)

OTHER PUBLICATIONS

Heim et al, "*Textile Heart Valve: Novel Shaping Process and Material Performances*", Materials and Manufacturing Processes, 26:1303-1309 2011.
(Continued)

*Primary Examiner* — Ann Schillinger
(74) *Attorney, Agent, or Firm* — Nixon & Vanderhye, P.C.

(57) ABSTRACT

The present invention provides a method of making a prosthetic valve that can take a first form wherein the valve is open and a second form wherein the valve is closed, the valve comprising a leaflet assembly having at least one leaflet attached to a supporting element, the leaflet having a free margin that can move between a first position wherein the valve takes the first form and a second position wherein the valve takes the second form, the method comprising providing a textile structure, and forming the leaflet assembly from the textile structure, such that a selvedge of the textile structure forms the free margin of the leaflet, wherein the textile structure is made by weaving warp and fill threads into a two-layer woven fabric having two stacked and
(Continued)

interconnected layers, the two layers having selvedges at one longitudinal edge, and wherein forming the leaflet assembly comprises connecting two lateral edges of a single piece of the fabric to make a substantially tubular structure wherein the inner layer forms the leaflet and the outer layer forms the supporting element. With this method a prosthetic valve can be made with little process variability and errors, and resulting in a valve with high reliability and durability. The invention also relates to a method of making a leaflet assembly, and to a leaflet assembly and a prosthetic valve obtainable by said methods.

12 Claims, 9 Drawing Sheets

(30) Foreign Application Priority Data

May 6, 2014 (EP) .................................. 14167271
May 6, 2014 (EP) .................................. 14167272

(58) Field of Classification Search
CPC ............... A61F 2/24; A61F 2210/0076; A61F 2240/001; A61F 2250/006
See application file for complete search history.

(56) References Cited

U.S. PATENT DOCUMENTS

| | | | |
|---|---|---|---|
| 4,035,849 A | 7/1977 | Angell et al. | |
| 4,191,218 A | 3/1980 | Clark et al. | |
| 4,610,688 A | 9/1986 | Silvestrini et al. | |
| 5,500,014 A | 3/1996 | Quijano et al. | |
| 5,800,514 A | 9/1998 | Nunez et al. | |
| 5,855,602 A | 1/1999 | Angell | |
| 6,283,995 B1 | 9/2001 | Moe et al. | |
| 6,454,799 B1* | 9/2002 | Schreck ............... | A61F 2/2418 623/2.1 |
| 6,726,715 B2 | 4/2004 | Sutherland | |
| 7,465,316 B2* | 12/2008 | Kujawski ............... | A61F 2/06 623/1.31 |
| 10,039,640 B2 | 8/2018 | Grundeman et al. | |
| 2003/0114924 A1 | 6/2003 | Moe | |
| 2004/0176658 A1 | 9/2004 | McMurray | |
| 2005/0027348 A1 | 2/2005 | Case et al. | |
| 2005/0137681 A1 | 6/2005 | Shoemaker et al. | |
| 2005/0177227 A1* | 8/2005 | Heim ............... | A61F 2/2412 623/2.12 |
| 2006/0085080 A1* | 4/2006 | Bechgaard ............ | A61F 2/30721 623/23.43 |
| 2008/0200977 A1 | 8/2008 | Paul et al. | |
| 2008/0275540 A1 | 11/2008 | Wen | |
| 2009/0276039 A1 | 11/2009 | Meretei | |
| 2011/0282440 A1 | 11/2011 | Cao et al. | |
| 2012/0172978 A1 | 7/2012 | DuMontelle | |
| 2013/0073037 A1 | 3/2013 | Gregg et al. | |
| 2014/0135906 A1 | 5/2014 | Winner et al. | |
| 2016/0038280 A1 | 2/2016 | Morriss et al. | |
| 2017/0065408 A1 | 3/2017 | Grundeman et al. | |
| 2017/0189172 A1 | 7/2017 | Grundeman et al. | |

FOREIGN PATENT DOCUMENTS

| | | |
|---|---|---|
| WO | 2004/032987 | 4/2004 |
| WO | 2010/020660 | 2/2010 |
| WO | WO 2010/020660 | 2/2010 |
| WO | 2012/177942 | 12/2012 |
| WO | 2013/013032 | 1/2013 |

OTHER PUBLICATIONS

Zaidi et al, "*Preliminary experience with porcine intestinal submucosa (CorMatrix) for valve reconstruction in congenital heart disease: Histologic evaluation of explanted valves*", The Journal of Thoracic and Cardiovascular Surgery, vol. 148, No. 5, pp. 2217-2225 (Nov. 2014).
http://www.cs.arizona.edu/patterns/weaving/webdocs/opr_rgdw. pdf (Oct. 5, 2002).
JP Application No. 2016-564324, Notice of Reasons for Rejection, dated Mar. 26, 2019.
JP Application No. 2016-564298, Notice of Reasons for Rejection, dated Apr. 2, 2019.
International Search Report and Written Opinion of the Isa for PCT/EP2015/059984, dated Jul. 7, 2015, 9 pages.
International Preliminary Report on Patentability for PCT/EP2015/059984, dated Aug. 2, 2016, 7 pages.

* cited by examiner

METHOD OF MAKING A PROSTHETIC VALVE AND VALVE OBTAINED THEREWITH

This application is the U.S. national phase of International Application No. PCT/EP2015/059984 filed 6 May 2015, which designated the U.S. and claims priority to EP Patent Application Nos. 14167271.7 filed 6 May 2014, 14167270.9 filed 6 May 2014, 14167269.1 filed 6 May 2014, and 14167272.5 filed 6 May 2014, the entire contents of each of which are hereby incorporated by reference.

GENERAL FIELD OF THE INVENTION

The invention relates to methods of making implantable medical devices and to such medical devices, like a prosthetic valve and more specifically a two- or three-leaflet prosthetic heart valve.

BACKGROUND

A typical natural valve of a mammal is the aortic valve, one of the four heart valves. The aortic valve comprises three leaflets, also called cusps, attached to the aortic root that serves as a supporting element for these leaflets. Each of the three leaflets of the aortic valve has a free margin and a margin where it is attached in semilunar fashion to the aortic root. When the valve opens, the leaflets fall back into their sinuses without the potential of occluding any coronary orifice. The hingelines of adjacent leaflets meet at the level of the sinutubular junction, forming at least part of the commissures. The body of a leaflet is pliable, extendable and thin to provide the required flexibility, although its thickness is not uniform. The leaflet is slightly thicker towards its free margin. On its ventricular surface is the zone of apposition, known as the lunule, occupying the full width along the free margin and spanning approximately one-third of the depth of the leaflet. This is where the leaflet meets the adjacent leaflets during valvular closure. With the valve in closed position, the margins of the lunules meet together, separating blood in the left ventricular cavity of the heart from blood in the aorta. For a valve of this type, or a corresponding type, highest mechanical stresses during opening and closing occur at the commissures and, to a lesser extent, at the free margin of the leaflets.

Prosthetic valves are implanted in the human or animal body and may for instance be used as a passive, one direction prosthetic valve within or nearby blood vessels. They can be completely preformed and implanted as such, or formed in situ using the artificial and/or natural parts needed to form a functional prosthetic valve. A suitable prosthetic valve needs to open and close readily in response to differential pressure on either side of the valve, cause no or only little non-physiological turbulence in the blood flow, and avoid too much regurgitation. Cardiovascular products, such as heart valve prostheses, are thus subject to high requirements with respect to loading conditions, both in magnitude as in number of cycles. Typically, heart valve leaflets may undergo over a billion load cycles in their lifetime. Durability of prosthetic valves, especially of moving leaflets, is therefore an important requirement.

Any prosthetic valve should be able to resist the actual mechanical load on the commissures and leaflet free margin during valvular operation and preferably, maintain to resist such cyclical load during many years. For this, not only initial strength is an important parameter but also reducing the chances of (non-apparent) production anomalies in making the valve.

Today, valves used in valve surgery typically are bioprosthetic valves having leaflets made from biological tissue, often chemically treated bovine pericardium. This is an elastic material that performs relatively well and is able to mimic the natural valve. However, early failure is often encountered, and is believed to be associated with high stresses on the leaflet material upon continuous stretching and retracting under pulsatile load. Various methods have been proposed as alternatives for making leaflets of prosthetic valves wherein synthetic materials and alternative designs are used.

A valve prosthesis made using synthetic fibers is for example described in NL1008349. This valve comprises a supporting element carrying a number of leaflets, which have been made by winding reinforcing fibers onto a mandrel in specific directions corresponding to the occurring stresses in the leaflets. Since the fibers have to be positioned according to the maximum stress lines, this valve prosthesis is difficult to make and uses many wound layers to accommodate stresses, whereby mass is added.

Similarly, U.S. Pat. No. 6,726,715 describes a leaflet for a heart valve comprising a flexible sheet having stress-relieving fibrous elements aligned with predetermined stress lines in the leaflet during valve operation. Sheet material is typically PTFE or PVF, with high-strength/high-modulus fibers as reinforcing elements. Fibers such as carbon, aramid, or polyethylene fibers like Dyneema® UHMWPE fibers may be used.

WO2010/020660 describes a prosthetic valve made from a uniform hollow braid made from polyolefin fibers. The hollow braid is shaped to form a valve by pulling it over a mould, comprising a tubular part and a star-shaped part. By subsequently applying heat and pressure, the hollow braid takes the shape of the mould and different sections are created. Around the tubular part of the mould the braid forms into a section that corresponds to a supporting element of the valve, whereas a star shaped part of the mould provides a section that corresponds to multiple valve leaflets. Before removing the valve from the mould, the front and back sides of the valve prosthesis are edge trimmed. To prevent disruption of the trimmed edge, the edge may be heat treated to melt fuse the yarns to each other, provided with a stitching, or otherwise treated to make the edge mechanically stable.

WO 2004/032987 concerns a medical device having at least three layers of polymeric components arranged in a sandwich construction, wherein the polymeric component of the middle layer has a shorter chain length than the other polymeric components. A heart valve is mentioned as a possible application of the sandwich construction.

Heim et al. (Materials and Manufacturing Processes, 26: 1303-1309, 2011) disclose a method wherein artificial leaflets are made from woven polyester yarns by thermally shaping the woven textile on a mould into a three-cusp geometry; showing that woven polyester could be suited to form a valve prosthesis. Polyester yarn has stretching properties such that the woven textile is able to mimic the natural elastic stretching of a human valve (about 15% of elongation), due to its typical elongation at break of about 14-17%. In order to obtain a valve with good contact between leaflets in closed position and to limit stresses during working cycles, the authors teach to shape the leaflets such that there is a fairly large inherent opening in the centre of the valve, whereas under cardiac pulsatile load adequate coaptation is created over the length of the free margin of the leaflets to prevent or at least minimize regurgitation.

In US2005/0137681 a venous valve with a tubular frame and a cover is disclosed, which cover includes surfaces defining a reversibly sealable opening and thus acting as leaflets. The leaflets can have various sizes and shapes, including arcuate edges, curved surfaces, a concave structure, or include a curved support structure to efficiently close the valve and restrict retrograde fluid flow. Leaflets may be made of biologic or synthetic fluid-impermeable material, including ePTFE, PET, urethane and polyethylene.

WO2000/62714 discloses a heart valve prosthesis including a one-piece moulded body with a plurality of leaflets, made from a silicone or polyurethane. In the neutral or rest position, the leaflets' free margins converge to form a non-uniform gap between them. The leaflets have a scallop in their free margins, proving sufficient material at the center to seal against reversed fluid flow with minimum coaptation.

US2004/176658 relates to a medical support net adapted to be placed around an organ; for example a cardiac support net, which is made as a multilayered fabric by a warp knitting technique, preferably from multifilament polyester yarn.

U.S. Pat. No. 4,191,218 discloses woven fabrics for use in vascular prostheses and heart valves, which fabrics are woven from multi-filament (polyester) yarns comprising filaments of about 10 µm diameter, and which fabrics are heat shrunk to result in open interstitial space of 20-40 µm and elongation in at least one direction of at least 10%. The fabrics preferably have a woven selvedge, which forms the free margin of a heart valve leaflet.

In US2005/177227 a method of making a cardiac valve prosthesis is disclosed, wherein a textile membrane, preferably made from polyester or PTFE, is shaped to form leaflets; for example by cutting out segments and using a shaped member reproducing the geometry of a cardiac valve in closed artery position, followed by thermofixation. It is indicated that a leaflet preferably has a woven or knitted free edge to avoid raveling.

US2012/0172978 describes a prosthetic valve comprising leaflets made from an isotropic filter screen material that has uniform pores of 15-60 µm and a thickness of 10-100 µm, and which material is woven from e.g. polyester or polypropylene monofilaments. In response to a closed flow pressure the leaflets can be pushed together to engage at the outflow edge. Methods of making such valve comprise steps of forming separately leaflets from a single layer of said screen material, coupling them together along an attachment line, and optionally coupling to a sewing ring or stent. The attachment line forms a commissure, optionally in combination with connected tabs extending from the ends of the free margin of leaflets at the outflow edge. Typically leaflets are cut from the screen material in such way that the edges of a finished leaflet do not substantially have any extending fibers.

Still, there is a continuing need for an efficient method of making implantable prosthetic valves having adequate properties for replacing a natural valve, especially for prosthetic valves showing very good durability.

SUMMARY

The present invention provides a method of making a prosthetic valve (400) that can take a first form wherein the valve is open and a second form wherein the valve is closed, the valve comprising a leaflet assembly having at least one leaflet (3) attached to a supporting element (2), the leaflet having a free margin (5) that can move between a first position wherein the valve takes the first form and a second position wherein the valve takes the second form, the method comprising:

providing a textile structure, and forming the leaflet assembly from the textile structure, such that a selvedge of the textile structure forms the free margin of the leaflet, wherein the textile structure is made by weaving warp and fill threads into a two-layer woven fabric having two stacked and interconnected layers, two layers having selvedges at one longitudinal edge, and wherein forming the leaflet assembly comprises connecting two lateral edges of a single piece of the fabric to make a substantially tubular structure wherein the inner layer forms the leaflet and the outer layer forms the supporting element.

In this method a single piece of a two-layer woven fabric is used for making a tubular leaflet assembly comprising at least one leaflet and supporting element, with the free margin of the leaflet being formed from a selvedge of the woven fabric. Prior methods typically make a leaflet assembly from multiple pieces of material, that are assembled and connected to each other. Such two-layer fabric can be made with a weaving technology commonly referred to as 'double weaving', which is typically applied for making decorative textile structures. Different connections can be made between the two layers in such process, including making a closed longitudinal edge to make a so-called double width fabric, and making further connections by crossing of warp and/or fill threads from one layer to the other. This allows making connections that (pre)define (adjacent) leaflets as sections in one layer attached to corresponding sections defining supporting elements in the other layer, in a mutual configuration desired for the leaflet assembly and ultimate valve. In addition, such integral connections may form part of the commissure in the valve. With this method a prosthetic valve can be made with little process variability and errors, and resulting in a valve with high reliability and durability. Considering the size of a valve for use in a bodily conduit like blood vessels or arteries, the width of a textile structure for making a leaflet assembly will be on the order of at most several centimeters. Such size may appear relatively small for (industrial) woven fabric production, but suitable weaving methods, weaving patterns and machinery are known in the art for such purpose; for example those generally referred to as narrow fabric weaving (systems) that are typically used for making tapes and ribbons. In such weaving equipment, typically movement of every warp thread can be individually controlled to make multiple layers, and various connections between layers. Further information on such weavings methods is available on the internet, for example on double weaving in the document available via http://www.cs.arizona.edu/patterns/weaving/webdocs/opr_rgdw.pdf. Such weaving methods also allow making fabrics with more than two layers. Analogously to the described method for making a prosthetic valve from a two-layer fabric, multi-layer fabric could be used wherein two of the layers are used for forming a leaflet layer and an supporting element layer. For example, an additional layer may have some other function, or supporting elements may comprise more than one layer.

The two-layer woven fabric may be made using various fibers and yarns as warp and fill threads; including high-strength yarns such as UHMWPE multifilament yarn, resulting in thin and flexible yet very strong layers in the woven fabric. Forming the valve may further comprise attaching the leaflet assembly to a stent, for example with stitches, to result in a strong and durable commissure at least at the connecting points between leaflet and stent at the outflow side of the valve, which are typically the places where most stress concentrates during valve opening and closure.

The invention also relates to a method of making a leaflet assembly, and to a leaflet assembly and a prosthetic valve obtainable by said methods, more specifically such prosthetic valve that can take a first form wherein the valve is open and a second form wherein the valve is closed, the valve comprising a leaflet assembly having at least one leaflet (3) attached to a supporting element (2), the leaflet having a free margin (5) that can move between a first position wherein the valve takes the first form and a second position wherein the valve takes the second form, wherein:

the leaflet assembly is made from a single piece of an at least two-layer woven fabric, which is made by weaving warp and fill threads into two stacked and interconnected layers, the two layers having selvedges at one longitudinal edge, and the leaflet assembly has a substantially tubular structure formed by connecting lateral edges of the piece of the at least two-layer woven fabric, wherein the inner layer forms the leaflet and the outer layer forms the supporting element and wherein a selvedge forms the free margin of the leaflet.

DEFINITIONS

A prosthetic valve is a constitution of at least one leaflet and supporting element, wherein the leaflet is attached to the supporting element such that the leaflet can flex or hinge to provide an open as well as a closed position for the valve, and may optionally comprise a rigid or semi-rigid support, also called frame or stent.

A leaflet assembly is the combination of at least one leaflet and corresponding supporting element in a generally tubular configuration, and may be made from multiple pieces of material connected together or from one single textile structure (like a woven fabric). The leaflet is the movable part and is attached to the supporting element, also called graft or skirt, and together they define pockets that can be filled with fluid to close the valve.

A commissure is generally a point or line along which two things are joined; in anatomy of natural heart valves a commissure is the distinct area of junction between two adjacent valve leaflets and their supporting vessel wall. Within the present application the commissure refers to the attachment line or region from the outflow side between a leaflet and supporting element in case of a stent-less valve, and between leaflet and stent, and optionally supporting element for a stented valve. In addition to connections forming a commissure, there can be further connections between leaflet, supporting element and/or stent, for example further defining leaflet shape.

A margin of a leaflet is an edge.

Coaptation means abutting, contacting or meeting of a leaflet and a closure surface, such as another leaflet, to close the valve; coaptation height refers to the height or length of coaptation measured from the free margin in longitudinal direction of the valve, i.e. towards the bottom of the leaflet.

The centre line of a leaflet is a hypothetical line from the free margin at the centre of the valve to the nadir at the bottom of the leaflet, that is the lowest point defining the leaflet by connections to the supporting element. In case of a non-symmetrical valve with for example three leaflets, it is the line from the contacting or coaptation point of the three free margins to the nadir.

The curvature height characterizes the curvature in the leaflet of a valve as the largest orthogonal distance between the centre line and a straight line connecting the free margin at the centre of the valve and the nadir.

The radius of curvature of a leaflet is the radius of a circle that best fits a normal section of the curved surface of the leaflet in closed valve position.

An elastic material is a material that is capable of returning to its original shape after being deformed.

To impose a geometry on an object means that the geometry of this object is established by the creation of the object, as opposed to a geometry that can arise due to external forces applied to the object after creation.

Inflow side or bottom side of the valve means the side where fluid enters the valve when it is in open position, the opposite side is referred to as outflow side or top of the valve.

For something to run parallel with another thing means that both things predominantly extend in the same direction.

The elongation at break of a specimen is the elongation of that specimen recorded at the moment of rupture thereof under an applied load, expressed as a percentage of its original length. For sheet material, the elongation at break is often also called elongation at rupture or elongation at fracture.

A yarn is an elongated body having a length much greater than the width of its cross-section, typically comprising a plurality of continuous and/or discontinuous filaments, said filaments being preferably aligned substantially parallel to each other.

Adjacent means adjoining or nearest in position.

A selvedge (or selvage) is an edge of a woven structure wherein the threads that run in a direction perpendicular to the edge of the structure are not extending from the structure as free ends, but are continuous at the edge by returning into the structure. Selvedges are typically formed in fill (also called weft) threads during a shuttle weaving process, but may also be made with other techniques or in warp threads.

BRIEF DESCRIPTION OF DRAWINGS

All figures herein are schematic drawings only and not necessary to scale, and may not show all features or components for clarity reasons. Like reference numbers in different figures refer to like features.

DETAILED DESCRIPTION

Figure 1A:
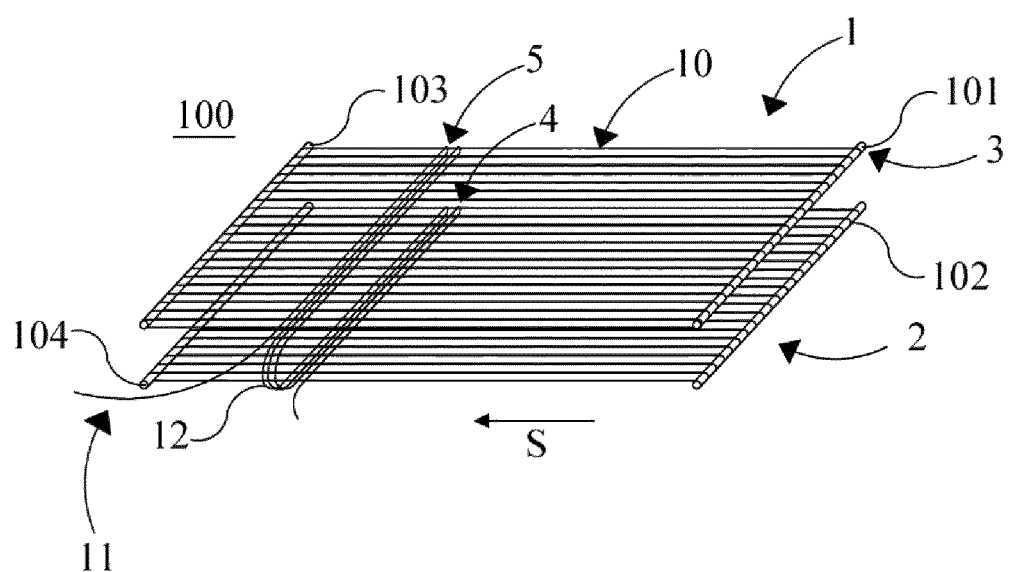
FIGS. 1A through 1I schematically show various steps for forming a valve prosthesis using a method according to the invention.

The prosthetic valve that is made with the method of the invention comprises one or more leaflets, which leaflets are formed in such way from a layer of the two-layer woven fabric that a selvedge of the textile structure forms the free margin of the leaflet. A selvedge is a self-finished or self-stabilised edge of a woven textile structure. A selvedge refrains the textile structure from unraveling or fraying at such edge, but—as opposed to other types of stabilised or finished edges—a selvedge is the result of the actual weaving process and not of an additional process step such as cutting, melting, gluing, stitching or other process for providing a stabilised edge. In a woven textile structure, selvedges typically (but not necessarily) run parallel to the warp threads and are formed by the fill thread(s) looping back into the fabric around the last warp thread after exiting. A selvedge is made inherently if fill threads are supplied endlessly as in a shuttle weaving process, but can also be made in a shuttle-less weaving operation by tucking-in the fringed ends of the fill threads after each interlacing and cutting. A further method is introducing additional threads with so-called leno selvedge design in the woven fabric, which will lock outermost thread ends at the edge. By having the selvedge to form the free-margin of the leaflet, this free margin is provided as an inherently mechanically stable edge without using an additional process step. Additional process steps like melting or sewing may complicate the manufacturing process of the valve as a whole, and also may give rise to side effects, like alteration of mechanical properties of the yarns or fabric. Nevertheless, such additional edge finishing may be suitably used to stabilise other edges of a woven textile structure for use in making a prosthetic valve; for example in case of making a continuous or endless woven fabric that later is to be cut into pieces of desired length (also simply called lengths) for forming e.g. leaflets. A suitable example of making a stabilised or finished edge is hot cutting of woven fabric, e.g. with a laser or with an electronic thermal cutter, also called hot knife, which allows simultaneously cutting and fusing fabrics of thermoplastic fibers in a controlled single step.

The prosthetic valve that is made with the method of the invention comprises one or more leaflets. Generally valves found in mammals, especially in the blood system, contain one, two or three leaflets; heart valves typically have two or three leaflets. In one embodiment a prosthetic valve is made that has two leaflets, with the second leaflet acting as a closure surface for the first leaflet and vice versa. In another embodiment the valve comprises three leaflets, each leaflet acting as a closure surface for the other two leaflets. Making prosthetic valves having more leaflets is likewise possible, but is more complex.

In methods described in prior art multiple woven textile structures, or pieces of woven textile structure, may be applied for forming a leaflet assembly comprising one or more leaflets and supporting elements. Such methods may comprise forming each leaflet and supporting element from separate pieces of woven textile structure and then assembling and connecting the various pieces together, e.g. by sewing or stitching to make seams, before or during attaching them to the stent. In the present method multiple leaflets and supporting elements are made from a single piece of woven textile structure. Suitable ways of forming a leaflet assembly from a single woven textile structure comprise providing a flat multilayer woven fabric, folding it and connecting ends to make a substantially tubular structure, and making optionally further connections between the layers to define and shape leaflets, before or during optionally attaching the assembly to a stent.

In the method of the invention a leaflet assembly is formed from a textile structure that is made by weaving warp and fill threads into a two-layer woven fabric having stacked and interconnected layers, wherein the two layers have selvedges at least at one longitudinal edge. The two longitudinal edges of the woven fabric run lengthwise in the fabric and thus parallel to warp threads. In an embodiment of the method a single piece of textile structure is provided for forming a leaflet assembly, which structure is made by a double weaving process resulting in a two-layer woven fabric that has two selvedges at one longitudinal edge—which is thus open- and a continuous connection or fold line at the opposite edge—connecting the layers into a closed edge-, and optionally further connections between the two layers. The fold line connecting the two layers is typically made by crossing the fill thread at such edge from one layer to the other.

In another embodiment of the method a single piece of textile structure is provided, which is a two-layer woven fabric that has two selvedges at both longitudinal edges—thus both being open—and further connections between the two layers to create different sections that (pre-)define leaflets in one layer and attached to supporting elements in the other layer, made by a double weaving process comprising crossing of threads at selected places between the two layers. The further connections generally pre-define leaflets as further defining steps may follow, for example during making the leaflet assembly and optionally during attaching the assembly to a stent; but may also fully define leaflets.

In the two-layer woven fabric made with above weaving methods one layer will form supporting elements and the other layer leaflets in the leaflet assembly. The lateral width of each layer can be determined during weaving a.o. by the number of warp threads in a layer, and both layers can be made to have the same or different width or size; for example by varying the number of warp threads in each layer. For example, the two layers in the fabric are made to have a different lateral width by using a different number of warp threads in the layers.

In another embodiment of the weaving process the length in longitudinal direction of the two layers, for example such length in a section between further connections, can be made to be the same, or to be larger in one layer than in the other layer by (locally) increasing the number of fill threads in one layer. For example, sections in the layer forming leaflets can be made larger than corresponding sections in the layer forming supporting elements. Such method can be used advantageously to create excess length of the free margin of a leaflet in the final valve, as will be discussed later. In such embodiment also a shape can be given to the leaflets during weaving; for example by locally changing thread density or weaving pattern.

In other embodiments further connections are made between the layers, for example to further (pre-)define leaflets in one layer and attaching to the other (supporting element) layer, by crossing threads during weaving or alternatively by providing stiches after weaving.

A two-layer woven fabric as described above can be made as a fabric of a distinct length in a dis-continuous process, for example on a loom with warp threads attached to beams, resulting in a single piece of fabric. A single piece of fabric can also be made in a continuous weaving operation by continuously feeding warp threads to warp beams, resulting in a continuous fabric, which is cut into pieces of desired length and cut edges are optionally stabilised. In both cases the obtained piece of fabric can be made into a tubular structure by connecting the fabric edges with warp (or cut) ends together, with the layer corresponding to supporting elements forming the outside and the layer corresponding to leaflets forming the inside of the structure. The warp threads in these embodiments run parallel to the free margin, which is a selvedge of the fabric (similarly for top edge of supporting elements).

The method of making a prosthetic valve may further comprise attaching the leaflet assembly to a stent, which may also at least partly coincide with further steps to better define and shape leaflets. This is further explained in accompanying illustrative Figures by making a three leaflet valve as example; but which may similarly apply to making other valves.

Figure 1B:
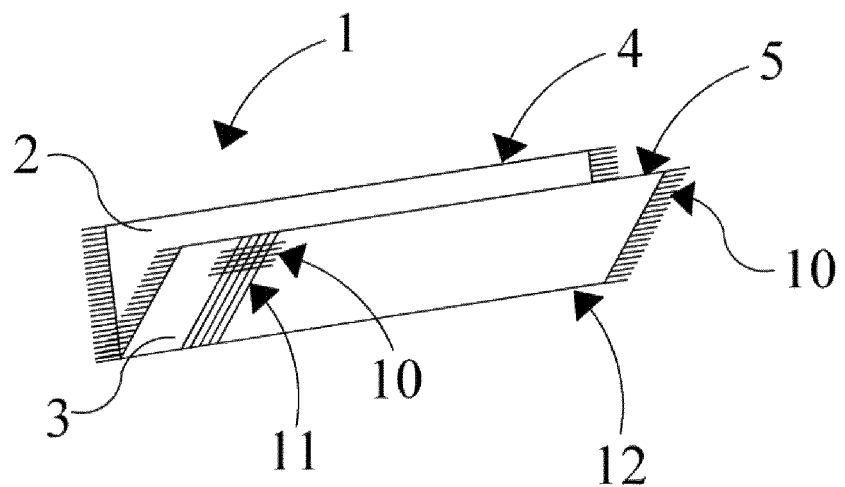
Figure 1:
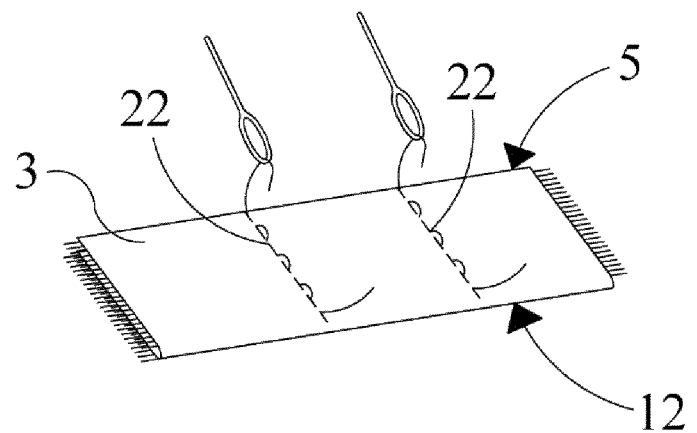

Reference is now made to FIG. 1, comprising subfigures 1A-1L, which schematically shows various steps of an embodiment of the method of forming a prosthetic valve. In FIG. 1A a weaving loom 100 is depicted, the loom having four warp beams (or loom bars) 101, 102, 103 and 104. Warp threads 10 are provided between the upper two warp beams 101 and 103, and between the lower two beams 102 and 104. This way a textile structure having two stacked layers can be formed in one weaving process, using one loom set-up. For reasons of clarity, common other parts of the loom, such as the heald frames (or harnesses) with heddles to separate with a predetermined pattern warp threads in one layer (or in both layers) to form a clear space (or warp shed) through which (a shuttle or pick carrying) the fill (also called weft) thread can pass, and the optional bat (or reed) for pushing the fill thread against the fell of the cloth, are not shown. Warp threads may be attached to the beams (typical for a discontinuous process), or may be continuously fed with beams 101 and 102 as guiding members, and 103 and 104 in such case representing a single fabric beam for receiving the two-layer fabric made. The fill thread 11 as shown in FIG. 1A is woven in the upper layer 3 of the textile structure 1 by interlacing the fill thread with each of the upper warp threads (e.g. forming a plain weave), and passes back at the edge 5 of layer 3 towards fold line 12, where it is woven in the lower layer 2 until it reaches edge 4 of this lower layer and then passes back towards fold line 12. Note that for clarity the fold line is made to look larger in the figure than in practice. This way, the edges 5 and 4 are formed as selvedges. The weaving process continues until the textile structure has the desired size. The result is a two layered woven textile structure comprising a first distinct layer 2 having a selvedge 4, and a second distinct layer 3 having a selvedge 5. Layer 2 is connected to layer 3 along the fold line 12, by fill threads passing from the one layer to the other. These layers 2 and 3 will form respectively supporting element and leaflets of the ultimate valve, and the fold line 12 may form a part of the connections between supporting element and leaflet. An alternate embodiment further includes interweaving of the layers 2 and 3 by crossing threads between layers other than at the fold line, to result in further connections and forming e.g. more sections in a layer, partly defining individual leaflets.

After the textile structure 1 is woven, it is released from the loom. FIG. 1B shows the resulting textile structure that is woven as a double weave (or double width) cloth, having distinct layers 2 and 3, each having a selvedge 4 and 5 respectively. The warp threads 10 extend over a little length outside of the actual textile structure at the non-selvedge edges. These edges may optionally be stabilised, at this stage or later.

In a next step, as depicted in FIG. 1O, stitches 22 may be added further connecting the layers 3 and 2 (next to fold line 12). By adding two lines of stitches 22 to this structure, layer 3 is divided in three separate sections corresponding to separate leaflets in the leaflet assembly and valve.

Figure 1D:
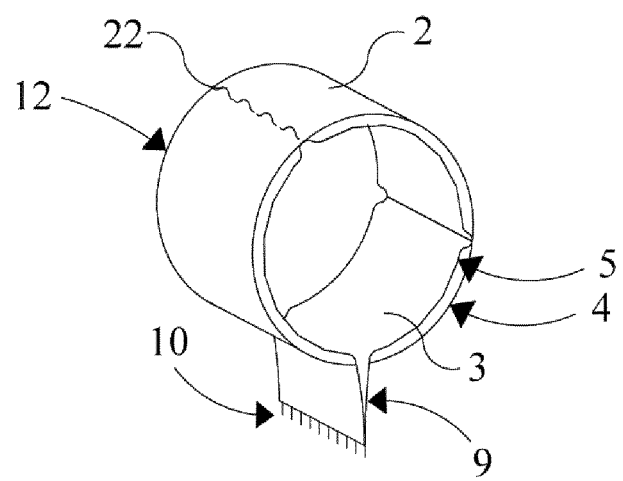
Figure 1E:
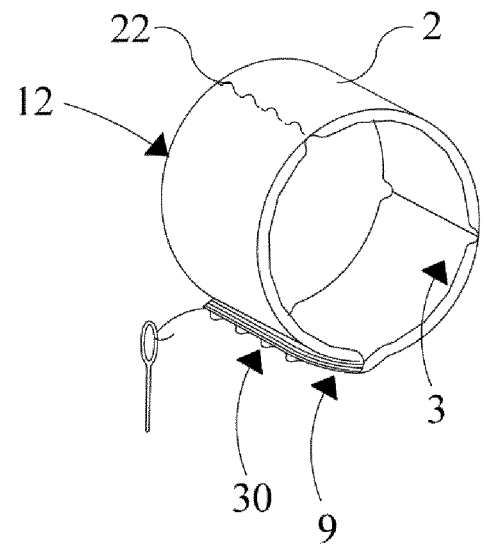

In a next step, as depicted in FIGS. 1D and 1E, the two lateral non-selvedge edges are brought together (i.e. the proximal end and distal end of the structure are configured on top of each other), such that the textile structure forms a tubular structure. As can be seen in FIGS. 1D and 1E, the leaflets of layer 3 are situated on the inside, while the supporting elements of layer 2 are situated on the outside of the structure. At the closure 9 of the loop, the warp threads 10 of both edges of the textile structure meet. Subsequently, the closure 9 of the loop is processed to make sure the closure can withstand the mechanical forces exerted on the prosthetic valve when in use. Firstly the loose warp ends may be cut and then, as can be seen in FIG. 1E, the closure 9 is folded towards the surface of layer 2 and thereafter secured with stitches 30, resulting locally in connected 4 layers. Alternatively, the folded ends are first rolled up and thereafter folded against layer 2, resulting locally in more than 4 layers. This way, any loose warp thread ends are no longer freely exposed, but a disadvantage may be that the rolled up closure 9 is somewhat thicker as compared to a non-rolled up closure. A further alternative is to stabilise the edges before connecting to layer 2.

Figure 1F:
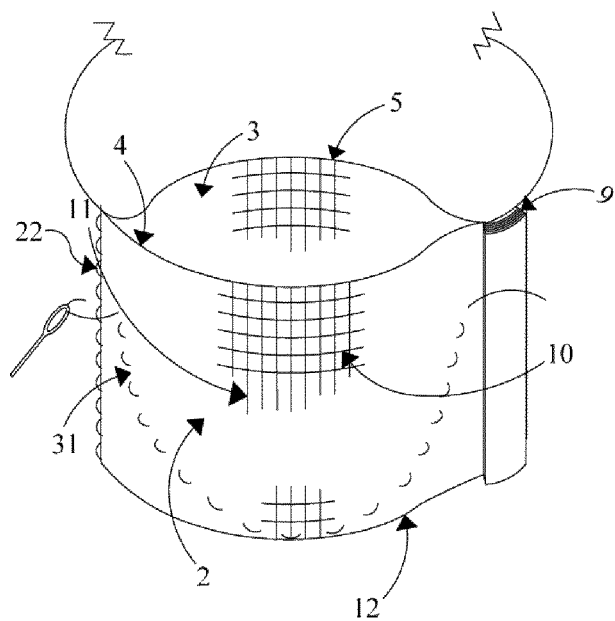

In a another step, as depicted in FIG. 1F, an additional stitch 31 is added, for example following a U-like line, which stitch further connects sections of layer 3 and corresponding sections in layer 2, to better define the leaflets or make a 3D-like shape. A segment of the tubular structure showing one combination of supporting element and leaflet is shown in FIG. 1F. As can be seen, the free margin of the leaflet is formed by selvedge 5. The connections made comprise, starting from the free margin, stitch 22 and stitch 31. This way, the leaflet and supporting element together form a pocket. By taking a position adjacent the supporting elements, the leaflets may open the ultimate valve, and by taking a position that extends away from the supporting elements, the leaflets may close the ultimate valve. These steps can likely be performed in the presence of a stent, also connecting the leaflet by stitches through multiple layers of woven fabric to the stent. For clarity reasons such stent is not shown here.

Figure 1G:
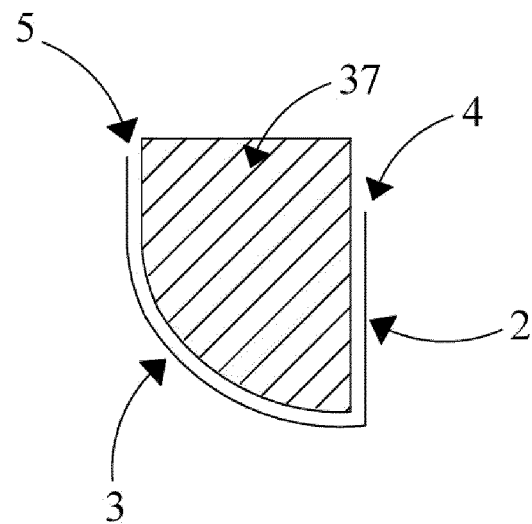

Referring now to FIG. 1G, in order to even better shape the leaflet and pocket a mould may be used. Before stitching connecting line 31, mould 37 may transpose the leaflet into shape, optionally by pulling the leaflet at edge 5 upwardly. This way, extra length is created between the nadir and the centre of the valve along the leaflet. Another way of creating such extra length is to already weave (sections in) layer 3 to be (locally) larger than layer 2 (for example as discussed in relation to FIG. 4). The steps as illustrated by FIGS. 1F and 1G can also be performed during or after connecting to a stent.

Figure 1H:
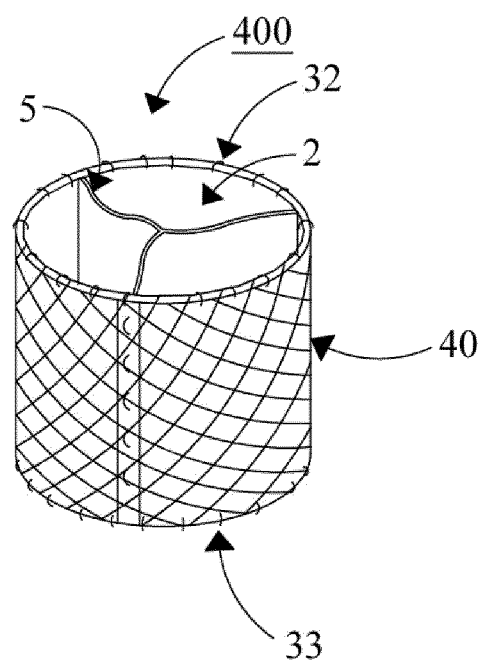
Figure 1I:
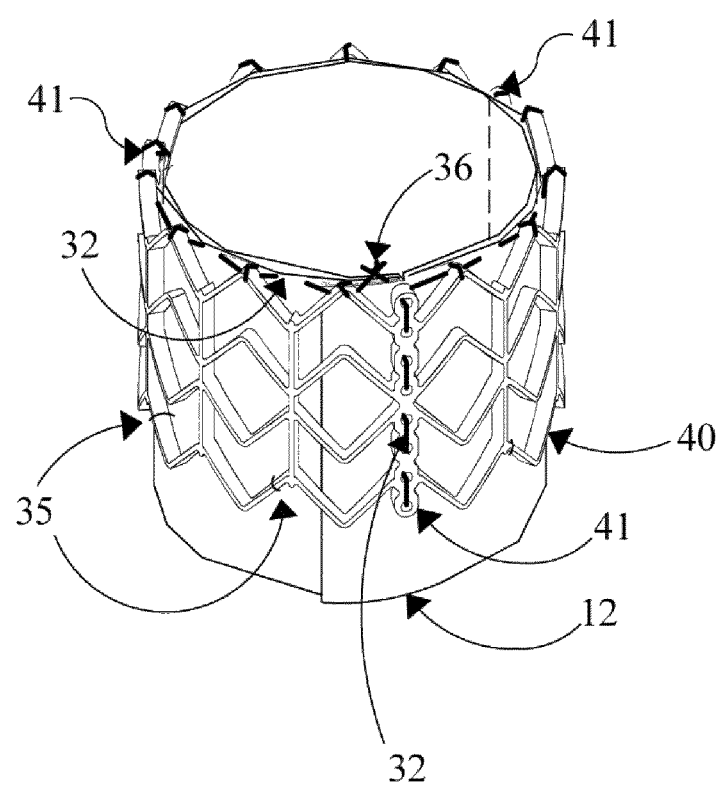

Referring now to FIGS. 1H and 1I, the textile structure or leaflet assembly made is connected to a circular wire stent 40 to make valve 400. The leaflet assembly is placed within the stent and may be connected at its bottom to the stent with stitches 33, and at the top with stitching 32 connecting only supporting elements 2. This stitching 32 preferably continues to connect the leaflets and supporting elements with the three stent posts 41 (see FIG. 1I), such connection further forming the final commissure. The free margins 5 of the three leaflets are also depicted in FIG. 1H. In this form, the valve 400 is closed by coaptation of the leaflets in neutral position. Would the free margins 5 be adjacent the supporting element 2 (i.e. adjacent the wall of stent 40), the valve 400 would be open. Some more details of the stent configuration and its posts 41 are depicted in FIG. 1I. Knot 36 is made in suture 30, as connecting point for suture 32. In an alternative approach, stitches 33 are made at this stage; then temporary connections 35 may be used to keep the structure in place during suturing to posts 41, and can be removed thereafter. FIG. 1I shows an alternate embodiment wherein the leaflet assembly extends from the bottom of the stent, and this part may in a further step be folded to the outside of the stent and connected thereto, forming a cushioning layer on the stent. An advantage hereof may be smoother fitting to a vessel or artery upon implantation.

In an alternative embodiment, instead of using stitches 22 early in the forming process (as shown in FIG. 1C), the woven textile structure as such (as shown in FIG. 1B) is tightly wrapped around the stent 40 (the stent at this stage being covered with a protective sheet of plastic) or another shaping member like a rod, and the four layers of the closure 9 are sutured together. Thereafter the stent is removed carefully, and the tubular textile structure is placed inside the stent. Then, stitches (sutures) corresponding to stitches 31, 32 and 33 are provided in order to form the leaflet cusps and secure the textile structure to the stent.

Figure 2A:
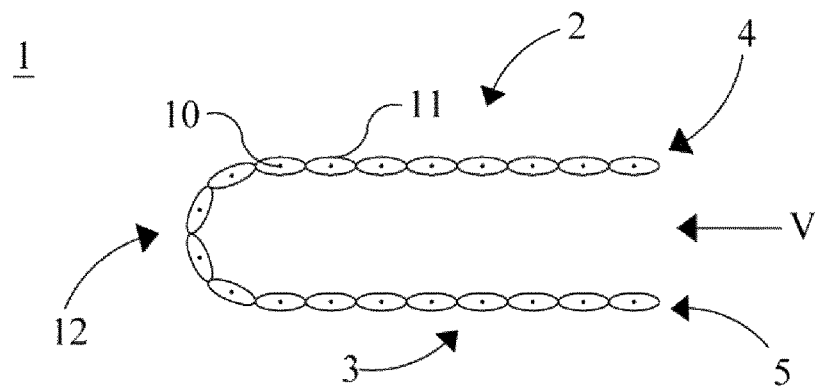
FIGS. 2A through 2C schematically show various views of a woven textile structure suitable for making a valve prosthesis.
Figure 2B:
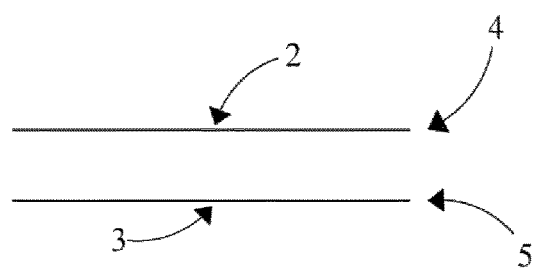
Figure 2C:
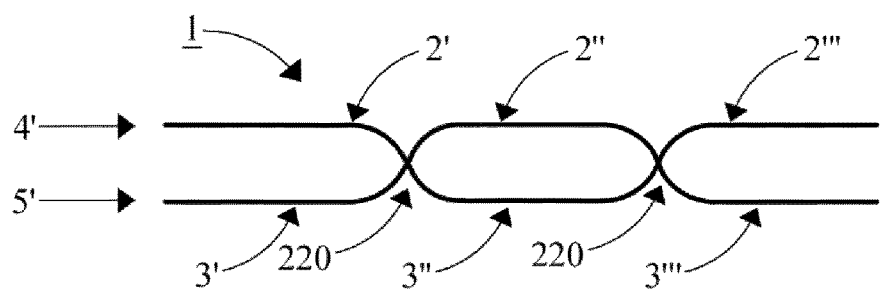

Referring now to FIG. 2, sub-figures 2A, 2B and 2C schematically show various views of a textile structure suitable for making a prosthetic valve. In the embodiment of FIG. 2A, a cross section parallel to the fill thread of the textile structure 1 in the direction S, as shown in FIG. 1A, is shown. As can be seen, the fill thread 11 is interlaced in layers 2 and 3 with each warp thread 10 to form a plain weave. By using the double weave method as depicted in FIG. 1, both layers 2 and 3 have longitudinal (i.e. parallel to the warp threads) selvedges 4 and 5 respectively. The fill thread, at fold line 12 passes from layer 2 to layer 3 and vice versa, thereby forming part of the connections between leaflet and supporting element. In FIG. 2B, a side view of this textile structure in the direction V as indicated in FIG. 2A is given. In this view, only the selvedges 4 and 5 are schematically depicted.

In an alternative embodiment, as depicted in FIG. 2C and representing a similar viewpoint as in FIG. 2B, the fill thread is interlaced with the warp threads in such way that cross lines 220 are formed as connections in the textile structure. The textile structure 1 now comprises in total 6 sections in the two layers, viz. sections 2', 2" and 2'" in the top layer and sections 3', 3" and 3'" in the bottom layer. At the left cross line 220, the four sections 2', 2", 3' and 3" coincide along a line that will correspond to part of the commissure of the ultimate valve. For this, warp threads pass from section 2' to section 3" and warp threads pass from section 3' to section 2", as controlled during weaving by the moving pattern of heddles and warp threads. This way not only a mutual configuration is obtained wherein each section corresponds with a supporting element or leaflet, but also, a leaflet-supporting element connection is formed as a direct result of the weaving process, and has similar strength as the fabric itself. This also means that less stitches need to be added to form the ultimate commissure, including attaching to a stent. A corresponding weaving process takes place at the right hand cross line 220. By connecting the ends of the structure obtained as depicted in FIG. 2C a tubular three-leaflet assembly is obtained.

Figure 3A:
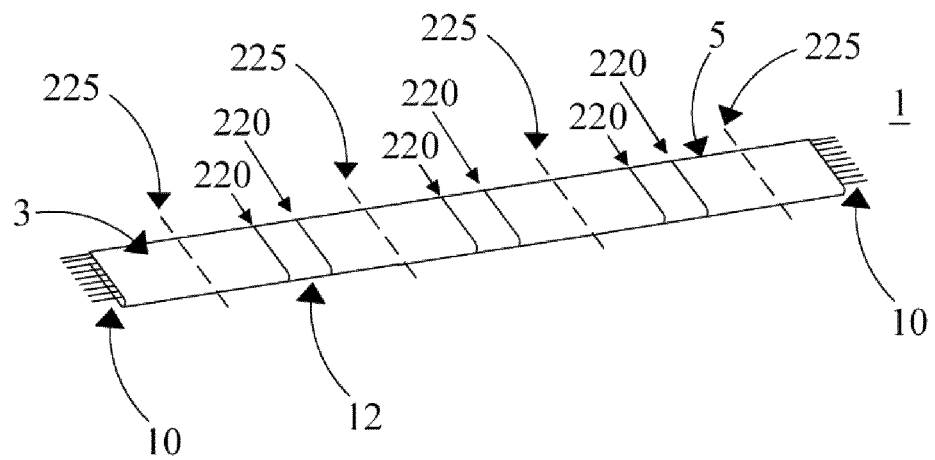
FIGS. 3A through 3C schematically show some steps in another embodiment of the invention.
Figure 3B:
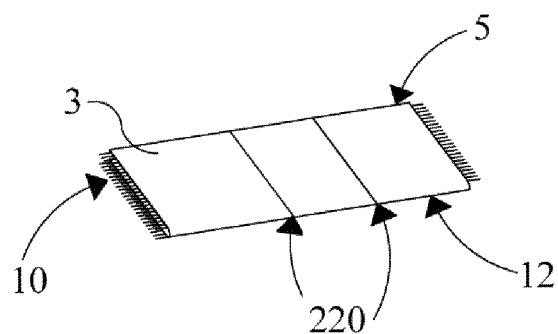
Figure 3C:
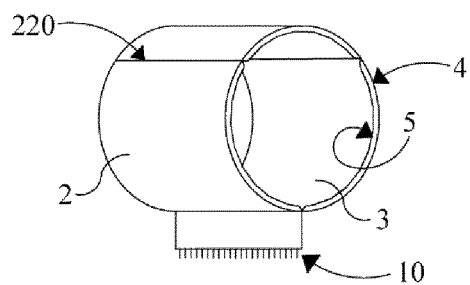

FIG. 3, consisting of sub-figures 3A, 3B and 3C, schematically shows various steps in another embodiment of a method according to the invention, based on crossing yarns technology as shown in FIG. 2C. In this embodiment the textile structure 1 is woven as a (semi-)continuous structure having multiple substructures, each substructure corresponding to one leaflet assembly to be formed. In FIG. 3A, each substructure is indicated as a structure between dotted lines 225. In this case, three substructures are depicted. In this view the selvedge 5 of layer 3 is at the top of textile structure 1, and the fold line 12 at its bottom. Layer 2 is underneath layer 3 and not further indicated. Each substructure is provided with two cross lines 220, defining sections. This way each substructure in itself corresponds to the textile structure shown in FIG. 2C. After weaving, the semi-continuous structure is cut along lines 225 into multiple pieces of textile structures as shown in FIG. 3B. Analogously to the process as illustrated in FIG. 1D, the substructure of FIG. 3B can be formed into a substantially tubular structure as shown in FIG. 3C. This structure can be further formed into a leaflet assembly and prosthetic valve, for example by using process steps corresponding to those of FIGS. 1E through 1I.

Figure 4A:
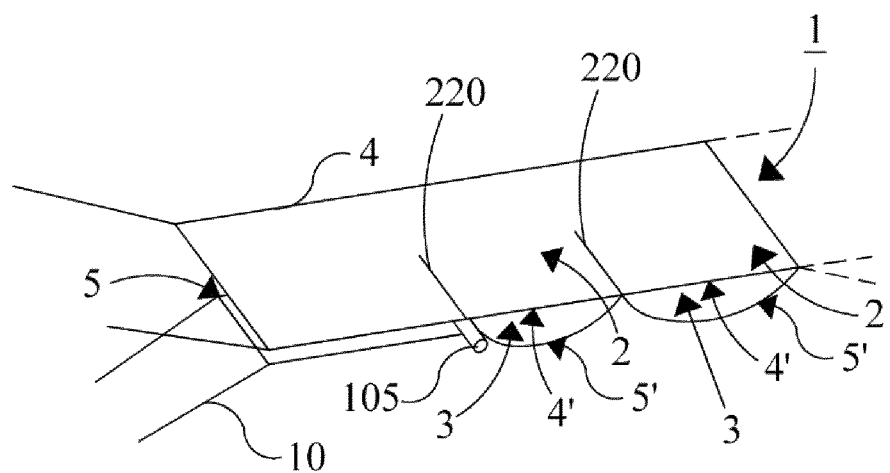
FIGS. 4A and 4B schematically show various steps in yet another embodiment of the invention.
Figure 4B:
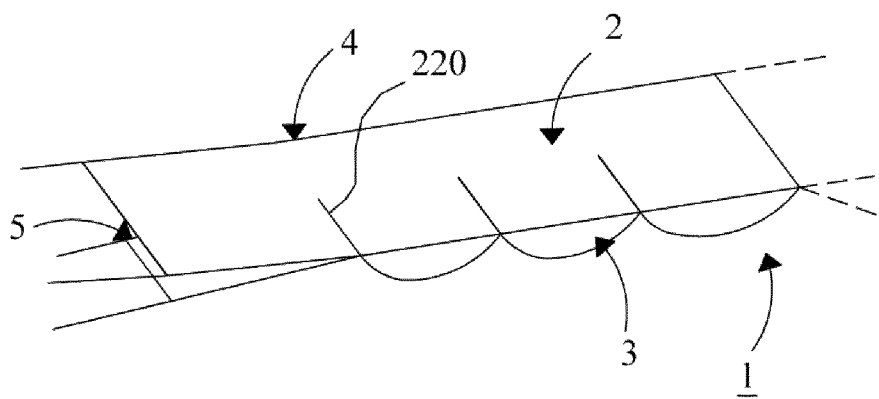

FIG. 4, consisting of sub-figures 4A and 4B, schematically shows a continuous woven structure produced according to another embodiment, a variation of the method as described in conjunction with FIG. 3. In this embodiment a textile structure 1 is woven with two fill threads, one for each layer, such that the top and bottom layers 2 and 3 have selvedges at both sides (4, 4', 5 and 5'). Layer 2 is made larger in width direction than layer 3 by using more warp threads; note that only at the edges warp threads 10 are depicted for both layers. In a leaflet assembly made from this structure, the supporting element will thus be longer then and extend away from the leaflets; and thus can be used for example to fold around a stent. The selvedges 5 or 5' may form the free margin of the leaflets in the resulting valve. In an alternative embodiment, the extending supporting element layer can be used to attach the leaflet assembly to the wall of a vessel or artery, thus functioning as a graft to (partly) replace or reinforce a weak or aneurysmal vessel. Such leaflet assembly, also without a stent, can thus function as a valve and as a graft, and may be called a valved graft or grafted valve. In such embodiment the outside of the leaflet assembly, the supporting elements layer, may be further treated to reduce permeability, e.g. by providing a coating or a further layer of material.

In the embodiment shown in FIGS. 4A and 4B the bottom layer is further extended with extra fill threads to increase the size of the leaflet and create excess length in the free margin. When the desired extra length for the leaflets is reached, layer 3 is pulled back with retaining bar 105 so that the fill line in the top layer is in line with the bottom layer as shown in FIG. 4A. The warp threads of the bottom layer and of the corresponding part of the top layer are than crossed to form cross line 220; also shown in FIG. 4B. These cross lines provide that a connection is made that will run—at least for the length formed by cross lines 220 starting at the free margin—in parallel with the longitudinal axis in the ultimate valve formed from structure 1 (corresponding to the method as outlined in FIG. 1).

As in FIG. 3, the obtained woven structure may be cut into pieces of desired length and having the desired number of sections to form leaflets (typically 3), be connected to form a tubular structure, and be optionally attached to a stent as described above. Alternatively, a structure may be woven wherein layer 3, i.e. leaflets is made to be larger than layer 2 (supporting elements).

The textile structure that is used in the method of the invention is made by weaving warp and fill threads into a two-layer woven fabric as discussed above. The weaving pattern applied during weaving the layers of the structure is not found to be particularly critical, and the skilled person will be able to select a pattern in combination with selected threads to obtain desired properties with some experiments. Typically, woven fabrics with commonly used patterns like plain, twill or basket weave, or combinations of different patterns are found to provide good performance. As also addressed later, the weaving pattern may at specific locations be different from the major part of the woven fabric, for example to make a non-flat shape in the leaflets. Other weaving patterns that could be applied locally may include so-called plain dutch weave, twilled dutch weave, reversed plain dutch weave and reversed twilled dutch weave.

In the method of the invention a two-layer woven fabric is used, which fabric comprises layers of such thickness and is woven with such warp and fill threads that a strong yet flexible and pliable fabric results, to enable high responsiveness of leaflets moving from open to closed positions in response of pressure differences over the valve, and effective closing by the leaflet abutting with a closure surface and forming sufficient coaptation. In an embodiment the fabric contains layers with single layer thickness of about 20-200 μm. Preferably layer thickness is at most 180, 150, 140, 130, 120, 110 or 100 μm and at least 30, 40, 50 or 60 μm for good performance. In embodiments the two-layer fabric contains layers with thickness between 40 to 150 μm, or having a thickness of between 50 to 100 μm.

In the method of the invention various types of fibers can be used as warp and fill threads, including natural or biological, as well as synthetic fibers. Threads may be formed from monofilament or multifilament yarn. More than one type of fiber may be used as warp and fill threads, and warp and fill threads may differ from each other. For making fabrics with uniform properties and less complicated production use of one type of fiber for warp or fill, or for warp and fill threads may be preferred. In an embodiment both warp and fill threads comprise at least 80 or 90 mass % of one type of fiber, and preferably consist essentially of one type of fiber. Suitable synthetic fibers include yarns made from polyesters like PET, from polyurethanes, or from polyolefins like PE or PP. In an embodiment the textile structure comprises yarns having an elongation at break of 10%. In a further embodiment the threads have a linear density of less than 120 dtex, preferably a linear density of less than 100, 80, 60, 50, 40, 30, 20 or even 15 dtex, preferably linear density of at least 5, 7, or 10 dtex; for example a linear density of between 5 and 30 dtex, or between 7 and 15 dtex. Applicant found that there are advantages in applying textile structures made from thin yarns for making a prosthetic valve regarding flexibility and responsiveness of the leaflets (note: although dtex is not a parameter that denotes actual dimension or spatial length, in practice it corresponds to yarn diameter since most synthetic and natural materials for making yarns have a density of about 1 kg/dm$^3$).

In another embodiment the warp and fill threads in the woven fabric comprise or are made from high-performance polymeric yarn, especially multi filament yarn having high tensile strength or tenacity of at least 1 GPa. Examples include carbon, aromatic polyamide, aromatic polyester, and ultra-high molecular weight polyolefin yarns.

In a further embodiment the warp and fill threads comprise ultra-high molecular weight polyethylene (UHMWPE) fibers, preferably the threads comprise at least 80 mass % of UHMWPE yarn, more preferably the warp and the fill threads substantially consist of UHMWPE multifilament yarn. Such yarns have been found to be ideally suitable for use in woven fabric for making leaflets and supporting elements of a valve prosthesis. The UHMWPE yarns are durable, can be made with the desired mechanical properties and a medical grade is commercially available, which medical grade is hardly immunogenic. In particular, it is preferred to use UHMWPE yarn that has an intrinsic viscosity (IV), of at least 5 dl/g, preferably at least 10 dl/g, more preferably at least 15 dl/g. Preferably, the IV is at most 40 dl/g, more preferably at most 30 dl/g, even more preferably at most 25 or 20 dl/g. IV is determined according to method PTC-179 (Hercules Inc. Rev. Apr. 29, 1982) at 135° C. in decalin, the dissolution time being 16 hours, with DBPC as anti-oxidant in an amount of 2 g/I solution, by extrapolating the viscosity as measured at different concentrations to zero concentration. Particularly preferred are gel-spun UHMWPE yarns, which typically have a Young's modulus of at least 30 or 50 GPa and a tenacity of at least 1 or 2 GPa. Tensile properties of UHMWPE yarn are defined and determined at room temperature, i.e., about 20° C., on multifilament yarn as specified in ASTM D885M, using a nominal gauge length of the fibre of 500 mm, a crosshead speed of 50%/min and Instron 2714 clamps, of type "Fibre Grip D5618C". On the basis of the measured stress-strain curve the modulus is determined as the gradient between 0.3 and 1% strain. For calculation of the modulus and strength, the tensile forces measured are divided by the titre, as determined by weighing 10 meters of yarns; values in GPa are calculated assuming a density of 0.97 g/cm$^3$. Preferably the yarn used comprises at least 80 or 90 mass % of UHMWPE filaments, or consists essentially of UHMWPE filaments. A preferred example of an UHMWPE yarn is Dyneema Purity® yarn obtainable from DSM, The Netherlands. This type of UHMWPE yarn is a medical grade yarn available in low dtex versions, the yarns typically having an elongation at break of about 2 to 4%. The ultra-high molecular weight polyethylene may be linear or branched, although preferably linear polyethylene is used due to the very high tenacity and modulus obtainable by stretching during manufacturing of the yarn. Linear polyethylene is herein understood to mean polyethylene with less than 1 side chain per 100 carbon atoms, and preferably with less than 1 side chain per 300 carbon atoms; a side chain or branch generally containing at least 10 carbon atoms. The number of side chains in a UHMWPE sample is determined by FTIR on a 2 mm thick compression moulded film, by quantifying the absorption at 1375 cm using a calibration curve based on NMR measurements (as in e.g. EP0269151).

Woven fabric made from such UHMWPE yarn provides good biocompatibilty to the prosthetic valve, and is very flexible, thus enabling fast response of the leaflet under pulsatile load. The flexible leaflets can also easily align with the supporting elements, thus creating an orifice approaching the dimensions of stent and supporting elements; also inducing less load on the commissure. Furthermore, it was found that the use of such thin yarns tends to lead to woven textile structures having relatively low pore size, and favourable blood compatibility. Durability of the valve may be further improved, for example by making stronger connections or attachments by stitching through multiple layers of fabric in forming a commissure, which is possible as the thin fabrics are flexible enough to allow folding of layers.

It is noted that use of such woven structure made from UHMWPE multifilament yarn is against the teaching of prior art to use a material that allows elastic stretching of about 15%, to mimic the stretch behaviour of natural leaflet material. As UHMWPE yarns typically have a low elongation at break and high resistance to stretching (high modulus), a woven fabric made therefrom will also be a relatively low-stretch material. It is believed to be a further advantage of the present method that use of such a textile structure may provide more durable leaflets and valve after implantation, not only from a mechanical point of view but also since stretching an object may induce collagen growing over this object. The low stretch characteristics of present leaflets thus reduce or even minimize the impetus of potential collagen or connected tissue overgrowth, that would otherwise result in leaflet thickening and loss of mobility and possibly induce focal thrombi or other vegetation. In general, tissue overgrowth or fibrosis may lead to leaflet compaction, which will result in valvular incompetence.

In the method according to the invention, stitches can be used to make the leaflet assembly as such and to attach it to a stent, a.o. to form the commissures. Such stitches are preferably made using a yarn or suture material that has similar strength properties as the yarn of the woven textile structure. In preferred embodiments, stitches are made using a yarn or a suture of suitable size or linear density, which comprises at least 80 or 90 mass % or consists essentially of UHMWPE yarn as defined above to ensure strong and durable connections and commissures.

In an embodiment a textile structure for forming leaflets and supporting elements is provided, which structure is made to have such size that after making connections a generally tubular leaflet assembly results wherein the free margins of the leaflets have at least the minimum length needed for closing the valve; i.e. for example the distance between the two ends of the free margin at the commissures via the centre of the valve in case of a substantially cylindrical assembly or valve having two or more leaflets. Preferably the free margin of a leaflet has excess length relative to said distance. In case the prosthetic valve further comprises a stent, the circumferential length and diameter of the leaflet assembly and supporting elements at least correspond to the internal dimensions of the generally circular tubular stent during use (that is after possible expansion upon implantation). For example, in case of a substantially cylindrical valve with internal radius R, and having three leaflets of same size that are attached to the supporting element with even distribution between commissures the needed minimum free margin length would be 2R. By making leaflets having at least the same size as the supporting elements their free margin length would be at least $2\pi R/3$; thus creating an oversize factor of at least about 1.05. Still more excess length can be obtained by forming oversized leaflets relative to actual size of the valve or its stent during use. This may be done during weaving the two-layer fabric, as already indicated above (FIG. 4).

In general it was found to be advantageous to make a prosthetic valve wherein the leaflet free margins have a total oversize or excess length factor of at least 1.05, preferably at least 1.07, 1.09, 1.11, 1.13 or 1.15, and preferably of at most about 1.4, more preferably at most 1.3, relative to the minimum length needed for closing the valve (for example relative to the minimum length needed to bridge the distance between commissures via the center of the valve). Stated otherwise, the free margins preferably have an excess length of at least 5%, more preferably of at least 7, 10 or 15%, and of at most 40 or 30%. Such excess length of free margins is found to aid in forming a relatively large closure surface between leaflets, that is in a significant coaptation height along the length of the free margins; and thus in effective closing of the valve upon reversed fluid flow and preventing regurgitation. A further advantage is that it is not needed to make a leaflet assembly that precisely matches the diameter of a stent (after optional compression), but an oversized leaflet assembly may be used in a range of different stents (depending on desired minimum excess length of the free margin).

In an embodiment the prosthetic valve comprises a leaflet that is made such that the leaflet, even without pulsatile load on the valve, can form a coaptation height of more than 0.1 mm along the length of the free margin. Preferably the coaptation height is at least 2, 3, 4 or 5 mm and at most 15, 13, 11, 10, 9, 8, or 7 mm, for example between 3 and 10 mm, preferably between 5 and 7 mm.

In another embodiment a geometry is imposed to the leaflet such that it has a convex surface, relative to fluid entering at the bottom of the valve, with a radius of curvature at the centre line of the leaflet of between 1 and 20 mm, for example 1, 2, 3, 4, 5, 6, 7, 8, 9, 10, 11, 12, 13, 14, 15, 16, 17, 18, 19 or 20 mm, preferably about 12 mm. It is believed that an imposed convex geometry with this particular small radius, as opposed to typical radii in known prosthetic valves of 50 mm or above, leads to less stress and deformation in the leaflet material and possibly less tension on the commissures. Such geometry also results in pockets defined by leaflet and supporting element with relatively large volume, which will be filled with fluid during closing. This may also promote effective reemptying upon opening, preventing e.g. blood remaining in a pocket and reducing risk of thrombus formation. Such 3D-like geometry may be obtained during weaving of the two-layer woven fabric, as for example by locally varying the number of fill threads, by locally changing the weaving pattern, or by locally changing thread density in the layer in the layer forming the leaflets, optionally in combination with other steps.

In another embodiment forming the leaflet assembly may further comprise a step of shaping a leaflet by contacting with a mould of desired shape, optionally heating the mould to a temperature of 3-60° C. (preferably 5-40° C.) below the melting point of the UHMWPE (see ISO11357-3 for a determination of the melting point of a polymer), optionally creep forming the textile structure (i.e. altering its dimensions), and submitting it to a controlled relaxation and/or plastic stretching to conform to at least a part of the mould. Such thermal forming process is for example described in WO2010/020660. With this embodiment a geometry is imposed to the leaflet, for example to create certain curvature or to meet certain clinical demands.

Figure 5A:
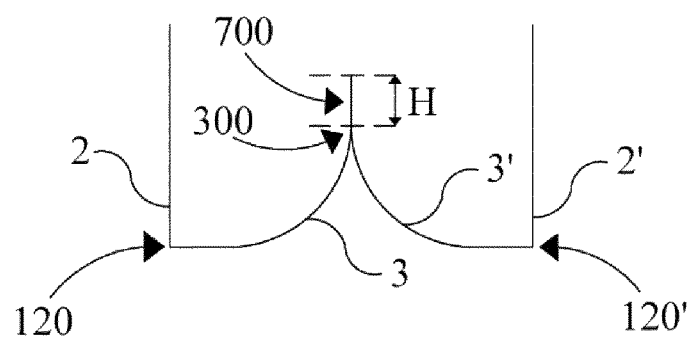
FIGS. 5A and 5B schematically show a cross sections of a valve with two leaflets.
Figure 5B:
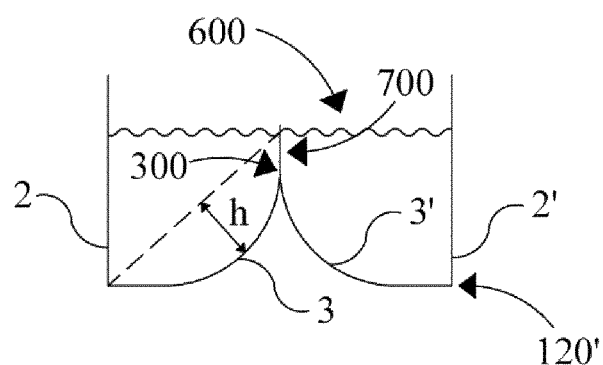

In FIG. 5A a cross section of a leaflet assembly for a prosthetic valve having two opposing leaflets is shown. The leaflets 3 and 3' have a geometry in neutral position without pulsatile load that enables them abut each other along the length of the free margin, thus also at the centre of the valve, and therewith form a coaptation 700 with a coaptation height H at this cross section. The coaptation height H extends with a minimum of 0.1 mm (the bottom of which is indicated with reference number 300) over the length of the free margin of each of the leaflets, possibly becoming even larger towards the commissures depending on commissure length. The geometry also comprises per leaflet a convex surface that extends between the top of the closure surface H and the respective connections to supporting elements, of which nadirs 120 and 120' are indicated. Each convex surface bulges away from the respective supporting elements 2 and 2'. In FIG. 5B it is shown that by a hydrostatic pressure, for example created by filling the pockets with water 600 as indicated, the imposed geometry and the coaptation height including formation of a closure "ribbon" having the length of the free margins can be inspected more easily and its dimensions estimated. It is noted that due to excess length of the free margin (more textile length then actually needed to span the distance between supporting elements and to coapt), it might be that at some spots when closing the valve by filling it with water, there is a wrinkle or small opening (a channel) in the closure surface. Such opening however is not persistent and will be closed in actual use by pulsatile load. Height h is the largest orthogonal distance between the line connecting free margin and nadir, and the curved surface of the leaflet.

In another embodiment the leaflet comprises a convex surface, wherein the height h at the centre line of the leaflet is more than 1 mm, preferably more than 2, 3 or 4 mm most preferably about 5 mm. A maximum value is inherently dependent on the outer dimensions of the valve itself, but is typically about 10-15 mm, for example 10, 11, 12, 13, 14, or 15 mm. This line section, when not being a (near-) perfect circle section, can, for the determination of its actual height h, be seen as a triangular section that begins at the free margin and ends at the nadir, and has as its top the leaflet bulge at the point most far away from the line between the begin and end. It is believed that an imposed convex geometry with this particular shape leads to less stress in the leaflet material and possibly less tension on the commissures.

In yet another embodiment the method further comprises steps of decreasing the permeability (for blood or other fluid) of at last part of the woven textile structure by applying a coating or optionally arranging the structure in a mould, heating to a temperature of 3-15° C. below the melting point of the yarn polymer, preferably UHMWPE, and holding at a temperature of 3-15° C. below the melting point for 10 seconds to 2 hours to impart a partial connection between adjacent filaments and/or yarns in the textile. Depending a.o. on the cross section of the yarns and their arrangement in the textile structure (for example type of weave), it can be advantageous to decrease the permeability of the textile structure.

The method of making a prosthetic valve may further comprise forming the valve by attaching the leaflet assembly to a stent. Such stent or frame is a rigid or semi-rigid structure typically comprising a rigid member, and often is of ring or cylindrical shape. Suitable materials for making a stent include rigid polymers, fiber-reinforced polymers, metals and their alloys, ceramics and combinations thereof. Suitable rigid polymers include polyacetals, dextroplast, polyurethane, polyethylene, polysulfones, polyethersulfones, polyarylsulfones, polyetheretherketones, and polyetherimides. Suitable metals include biocompatible metals, such as, stainless steel, titanium, cobalt alloys, such as Elgiloy®, a cobalt-chromium-nickel alloy, and MP35N, a nickel-cobalt-chromium-molybdenum alloy, and Nitinol®, a nickel-titanium alloy. In addition, stents can be produced from ceramic materials, such as pyrolytic carbon, silicon carbides or metal carbides, hydroxyapatite and alumina. Suitable stents can also be produced from carbons such as graphite. Preferably, a stent is at least partly made from a super elastic alloy, or a shape memory alloy, such as Nitinol®, that is available as a super elastic material, as well as a shape memory alloy. Such a stent allows to easily insert the valve prosthesis into the body in a desired position. Before insertion, the self-expandable stent is brought to a first (relatively low) temperature at which it has a compact configuration. This compact configuration allows to easily insert the stent (and the valve in conjunction therewith) into the body, using minimal invasive surgery. After positioning the stent, the shape memory alloy will heat up to the body temperature and change phase, thereby changing its shape into a larger diameter. For Nitinol® for instance, a phase change will occur between an austenitic phase and a martensitic phase. As a result the stent will expand and thereby create a clamping force against surrounding tissue. In another configuration, Nitinol® is super elastic and can be elastically deformed up to material strains of about 10%, thus deformation of a valve towards a compact shape is possible, still allowing elastic deployment to the final shape after placement.

The invention also relates to making a leaflet assembly as described above, and to a leaflet assembly and a prosthetic valve obtainable with or obtained by the above described methods, more specifically such prosthetic valve as defined in the embodiments listed below and by the claims.

The invention will now be further illustrated using the following non-limiting experiments.

Example 1

This example describes making a prosthetic valve according to the invention, and experiments wherein such valve is tested in vitro and used as a pulmonary valve prosthesis by implanting in sheep. In this example, each valve is made with the method described below, which is basically corresponding to the method as described in connection with FIG. 1 and FIG. 3B.

A woven fabric as shown in FIG. 1B was made from Dyneema Purity® TG 10 dtex UHMWPE multifilament yarn (available from DSM, The Netherlands) with a density of 458 warp yarns per inch and 223 fill yarns per inch. The folded two-layer structure had a length of 90 mm and a width of 21.5 mm, a layer thickness of 0.00314 inches (80 µm), and was woven as a 2 by 2 twill weave, with longitudinal selvedges. The cylindrical stent used has the design as shown in FIG. 1I, and was made of electromagnetically polished stainless steel 304. It had an outer diameter of 25 mm, an inner diameter of 23 mm and a height of 17 mm. For the stitches, two kinds of suture thread was used: Maxbraid PE 3-0 suture blue with tapered needles (available as MPC 900252 from BIOMET MERCK LTD), here beneath referred to as Suture A, and Maxbraid PE 4-0 suture blue with tapered needles (available as MPC 900244 from the same supplier), here beneath referred to as Suture B. Both sutures comprise UHMWPE yarn.

The pulmonary valve was made as follows. In order to create a coaptation height of 6 mm over the length of the free margins of the leaflets, extensive free margin length was created. The free margin length was oversized by following steps:

1. The leaflet free margin length in the textile structure as woven will be inherently equal to the supporting element length, the two layers having the same length. The distance between the edge of the supporting element formed as a cylinder and the middle of the valve being its radius R, the total length needed for 3 leaflets bridging this distance is 6R, whereas the length of the supporting element is 2πR. This creates an inherent excess length factor for the leaflet of 2πR/6R=1.05.
2. The two layer woven fabric is initially wrapped around (i.e. to the outside of) the 25 mm stent and the ends perpendicular to the free margin of the leaflets are sutured together. Subsequently the cylindrical textile structure is placed inside the stent of inner diameter 23 mm and fixed to the stent with UHMWPE sutures. This creates an excess length factor of 25/23=1.09.
3. In this example the final prosthetic heart valve size is 23 mm for implantation, therefore the stent of 25 mm outer diameter is radially compressed to 23 mm. This way the inside diameter of the stent where the supporting element and leaflet is fixed to is reduced from 23 mm to 21 mm. This creates an excess length factor of 23/21=1.10.

The total excess length factor of leaflet free margins created this way is $\pi \times 25/3 \times 21 = 1.25$. The excess length thus created is about 25%.

As indicated here above, the woven fabric is tightly wrapped around the stent, initially being used as mold, and the four layers at the closure (corresponding to 9 in FIG. 1D) are sutured together with Suture A starting at the outflow side of the fabric/stent combination by creating a knot 36, leaving about 2 cm loose end and a long end which is used to create a stitch line towards the inlet side of the fabric/valve combination. The stent/mold is removed carefully, and the tubular textile structure is placed inside the stent. The orientation of the warps of the leaflets and supporting element are perpendicular to the longitudinal central axis of the stent and commissural stent posts, ergo the fill yarns are in parallel to the central axis and commissural stent posts. The Suture A is then guided across fringe and stent post holes from inlet side towards outlet side (as shown in FIG. 1I), thus fixing the stent post 41 to the supporting element and leaflet at a length of about 9 mm. At the top of the post (outflow side) suture A is used to fix the edge of the supporting element to the stent in a continuous way by taking locked bites at the bended ends of the stent (the commonly known "Method of Blalock" using a festooning suture line). The end of the suture A is tied to its beginning at knot's 36 loose end. The textile structure is temporarily fixed to the remaining commissural stent posts 41 in a 120 degree fashion thus dividing it in three parts with about the same free margin length, to keep the structure in place during next steps; after which the temporary fixations can be removed.

A second suture B is used to complete attaching of the textile structure and create the actual leaflet assembly within the stent, by stitching to the two remaining stent posts 41 with a length of about 9 mm, and by stitching leaflet layer to the supporting element layer and stent to create the valve cusps. Prior to suturing, the free margin of all three individual leaflets were pulled up 3 mm in the middle of the free margin at the expense of length of the supporting element at the inflow side thus creating an arch of woven fabric between commissural posts elevated over the plane of the stent outflow side. Together with the aforementioned excess length this results in about 6 mm coaptation height in the center of the heart valve, and is likely even higher towards the commissures of about 9 mm. A mold (a negative form taken from a human aortic valve) is used for further sizing and shaping the belly of the leaflet as shown in FIG. 1G. The leaflet assembly is temporarily sutured (35) in the middle between the posts at the inflow side to maintain this configuration during next step. From this point suturing is started according to FIG. 1I. At the top of the post the leaflet and supporting element are taken double with two encircling bites. The leaflet sheet is pulled a little bit backwards over the top of the stent and is fixed by the suture. The course of the suture line of the leaflets (U-shaped) is also guided by the shapes of the stent and mold. The end of the suture is tied to the loose end left at the knot of the beginning of suture B. The resulting leaflets had a convex surface at the centre line of these leaflets with a radius of curvature of about 12 mm without pulsatile load. This was estimated to represent a distance h as depicted in FIG. 3C along the centre line with a height h of about 5 mm. The textile structure extends a few millimeter from the stent at the inflow site, as also shown in FIG. 1I, which can be used to attach the valve to vessel or artery wall upon implantation. The leaflet assembly is further connected with sutures to the lower part of the stent, and the temporary sutures 35 are removed.

After this fixation of leaflet assembly, the stent 40 of the valve is compressed from 25 mm diameter to 23 mm diameter and sterilized by using ethylenoxide sterilization.

Performance of valves made as described above was tested both in vitro and in vivo. Mechanical and functional testing of the prosthetic heart valve was performed in a simplified mock circulation. A BVS 5000 circulatory assist device (Abiomed, Danvers, Mass., USA) was included in a closed loop circuit having a reservoir and a return conduit. The heart pump bladder was driven by an Intra Aortic Balloon Pump (Maquet, Rastatt, Deutschland) with a frequency of 80 beats/min and output of 3600 cc/min, while afterload at the outflow side of the heart pump was set to 80 mmHg using a water column. In an initial test the standard valve of the heart pump at the outflow side was replaced by a valve constructed with three single leaflets made from woven fabric of 55 dtex UHMWPE yarn mounted in a transparent plastic conduit to study its open and closure behavior. This pilot valve sustained over 4 weeks (3.571.200 cycles) while remaining competent without deterioration of the woven leaflets. Build on this experience, a valve constructed as above (based on leaflets from woven fabric of 10 dtex UHMWPE yarn), was tested under equivalent physiologic loading conditions of the systemic human circulation, cumulatively during over 120 days (13.824.000 cycles). The valve opened fully into an optimal effective orifice, having commonly known vertical position of vibrating leaflets in parallel to the fluid stream, and closed while visually not revealing closure defects along the coaptation line of meeting free margins of leaflets, except from a tiny central hole of about 0.5 mm. Visual inspection after testing revealed a completely intact valve geometry; leaflets showing no fraying at the free margin or any other disruption or defects. All the suture lines as described above, as well as the knots were intact.

The prosthetic pulmonary valves were also implanted in adult sheep models (bread "swifter", body mass 55-70 kg) on the beating heart, while using an extra-corporeal circulation machine. Access to the pulmonary artery was achieved through left thoracotomy 3rd-4th i.c.s. The pulmonary artery was incised longitudinally, whereafter the native leaflets were cut out. Three positioning stitches of 5-0 Prolene® were used to pull on the commissural native posts. The valve was sutured into the pulmonary artery on the supra annular level (plane top of native commissures) using 5-0 Prolene®. The pulmonary artery was closed in linear fashion.

Echocardiography showed normal leaflet function without valvular or paravalvular regurgitation, apart from some occasional minimal regurgitation in the centre of the valve. The wound was closed and the sheep was taken to stables for recovery.

All treated sheep remained stable, without any adverse clinical signs up to 6 months observation periods. After this period the leaflet function was assessed again. Echocardiography showed adequate leaflet function with minor to moderate valvular but no paravalvular regurgitation, and there was no change in effective orifice since the day of implant. After this, the valves were taken out of the sheep for inspection. The leaflets and supporting elements were overgrown with tissue, but this appeared to be a very thin layer of fibroblasts and endothelial cells without histological and radiological signs of tissue calcification, and with a maximum thickness (including the leaflet) of 250 µm at the free edge with increasing amount of streamlining repair tissue towards the nadir. The mechanics of the valve appeared to be unaltered, all sutures were in place without fractures and the free margin of the leaflets appeared to be completely intact as originally made. No signs of fraying or other anomalies could be detected. The inventors are not aware of other studies using a prosthetic valve having leaflets made from a fabric woven from synthetic fibers, and wherein animals having such implanted valve survived a 6 months period without complications.

Example 2

A prosthetic aortic valve to be implanted in the systemic circulation was made analogously to Example 1 with some modifications. The supporting element was prepared by taking out three half-moon pieces of fabric (facing the sinus valsalva in the human or animal aorta) to allow blood supply to flow into the coronary ostia. The remaining edge of the supporting element was fixed to the leaftlet according to corresponding suture line of the U-shaped cusp suture line (facing the sinus valsalva). A second suture was used to complete attaching of the textile structure and create the actual leaflet assembly within the stent, by stitching to the stent posts 41 with a length of about 9 mm, and by stitching the leaflet layer to the supporting element layer and stent to create the valve cusps.

The valve was subsequently constructed in similar way as the pulmonary valve described here above. When completed, an additional sewing cuff of braided UHMWPE yarn was sutured with MaxBraid™ 3-0 UHMWPE (available from Teleflex, Limerick, Ireland), in an everted fashion using the Blalock stitch configuration.

Valves were implanted in adult sheep models (bread "swifter", body mass 65 kg) on the arrested heart under support of extra-corporeal circulation. Access to the aortic root was achieved through left thoracotomy 3rd-4th i.c.s. The pulmonary artery was dissected and pulled aside to allow transverse incision of the aorta. Classical implant was performed under cardiac arrest using a running suture Prolene® 5-0. The aorta was closed with a pericardial patch and the heart was defibrillated thereafter. The heart lung machine was disconnected. Echocardiography showed normal leaflet function without valvular or paravalvular regurgitation.

Any one of the embodiments, aspects and preferred features or ranges as disclosed in this application and relating to a method of making a prosthetic valve or a valve as obtainable by or as obtained with the method may be combined in any combination, unless otherwise stated herein or if clearly not feasible to a skilled person. The invention is further summarized in the below set of embodiments.

A method of making a prosthetic valve (400) that can take a first form wherein the valve is open and a second form wherein the valve is closed, the valve comprising a leaflet assembly having at least one leaflet (3) attached to a supporting element (2), the leaflet having a free margin (5) that can move between a first position wherein the valve takes the first form and a second position wherein the valve takes the second form, the method comprising:
 providing a textile structure,
  forming the leaflet assembly from the textile structure, such that a selvedge of the textile structure forms the free margin of the leaflet,
wherein the textile structure is made by weaving warp and fill threads into a two-layer woven fabric having stacked and interconnected layers, the two layers having selvedges at one longitudinal edge, and wherein forming the leaflet assembly comprises connecting two lateral edges of a single piece of the fabric to make a substantially tubular structure wherein the inner layer forms the leaflet and the outer layer forms the supporting element.

The method according to previous embodiment, wherein the prosthetic valve has one, two or three leaflets; preferably the valve has two or three leaflets, more preferably three leaflets.

The method according to previous embodiments, wherein the two layers in the fabric have two selvedges at one longitudinal edge and a continuous fold line at the opposite edge, and optionally further connections between the two layers.

The method according to any one of previous embodiments, wherein the two layers in the fabric have two selvedges at both longitudinal edges and further connections between the two layers to create different sections that pre-define leaflets in one layer.

The method according to any one of previous embodiments, wherein the two layers in the fabric are made to have a different lateral width by using a different number of warp threads in the layers.

The method according to any one of previous embodiments, wherein the two layers in the fabric are made to have a different length in longitudinal direction by locally increasing the number of fill threads in one layer, preferably sections in the layer forming leaflets are made larger than corresponding sections in the layer forming supporting elements.

The method according to any one of previous embodiments, wherein the single piece of fabric is made in a continuous weaving operation as a continuous fabric that is cut into pieces of desired length, and optionally cut edges are stabilized.

The method according to any one of previous embodiments, wherein the fabric is made with plain, twill or basket weave pattern.

The method according to any one of previous embodiments, wherein the fabric is made to impose a 3D geometry by locally changing weave pattern or weave density.

The method according to any one of previous embodiments, wherein the fabric contains layers with single layer thickness of about 20-200 μm, preferably layer thickness is at most 180, 150, 140, 130, 120, 110 or 100 μm and at least 30, 40, 50 or 60 μm, for example between 40 to 150 μm, or having a thickness of between 50 to 100 μm.

The method according to any one of previous embodiments, wherein warp and fill threads comprise at least 80 or 90 mass % or consist essentially of one type of monofilament or multifilament yarn.

The method according to any one of previous embodiments, wherein the warp and fill threads have a linear density of less than 120 dtex, preferably of less than 100, 80, 60, 50, 40, 30, 20 or even 15 dtex, and preferably of at least 5, 7, or 10 dtex; for example a linear density of between 5 and 30 dtex, or between 7 and 15 dtex.

The method according to any one of previous embodiments, wherein the warp and fill threads in the woven fabric comprise or are made from high-performance polymeric yarn, preferably multi filament yarn having tensile strength or tenacity of at least 1 GPa The method according to any one of previous embodiments, wherein the warp and fill threads comprise ultra-high molecular weight polyethylene (UHMWPE) yarn.

The method according to previous embodiment, wherein the UHMWPE yarn is a gel-spun UHMWPE multifilament yarn having a Young's modulus of at least 30 GPa or 50 GPa, a tenacity of at least 1 or 2 GPa, and preferably an elongation at break of about 2 to 4%.

The method according to previous embodiments, wherein the UHMWPE yarn comprises at least 80 or 90 mass % of UHMWPE filaments, or consists essentially of UHMWPE filaments.

The method according to any one of previous embodiments, wherein the free margin of a leaflet has excess length, relative to the minimum length needed for closing the valve, of at least 7%, preferably of at least 10 or 15%, and of at most 40 or 30%.

The method according to any one of previous embodiments, wherein the prosthetic valve comprises a leaflet that is made such that the leaflet, even without pulsatile load on the valve, can form a coaptation height of more than 0.1 mm along the length of the free margin, preferably the coaptation height is at least 2, 3, 4 or 5 mm and at most 15, 13, 11, 10, 9, 8, or 7 mm, for example between 3 and 10 mm, preferably between 5 and 7 mm.

The method according to any one of previous embodiments, further comprising attaching the leaflet assembly to a stent, preferably the stent is a self-expandable stent.

A method of making a leaflet assembly for a prosthetic valve as described in any one of the previous embodiments.

A leaflet assembly for a prosthetic valve as obtainable by the method according to previous embodiments.

A prosthetic valve as obtainable by the method according to any one of previous embodiments.

A prosthetic valve (400) that can take a first form wherein the valve is open and a second form wherein the valve is closed, the valve comprising a leaflet assembly having at least one leaflet (3) attached to a supporting element (2), the leaflet having a free margin (5) that can move between a first position wherein the valve takes the first form and a second position wherein the valve takes the second form, wherein:
 the leaflet assembly is made from a single piece of a two-layer woven fabric, which is made by weaving warp and fill threads into two stacked and interconnected layers, the two layers having selvedges at one longitudinal edge, and
 the leaflet assembly has a substantially tubular structure formed by connecting lateral edges of the piece of fabric, wherein the inner layer forms the leaflet and the outer layer forms the supporting element and wherein a selvedge forms the free margin of the leaflet.

The prosthetic valve according to previous embodiment, wherein the valve comprises two leaflets, the second leaflet acting as a closure surface for the first leaflet and vice versa, preferably the valve comprises three leaflets, each leaflet acting as a closure surface for the other two leaflets.

The prosthetic valve according to previous embodiments, wherein the two layers in the fabric have two selvedges at one longitudinal edge and a continuous fold line at the opposite edge, and optionally further connections between the two layers.

The prosthetic valve according to any one of previous embodiments, wherein the two layers in the fabric have two selvedges at both longitudinal edges and further connections between the two layers creating different sections that predefine leaflets in one layer.

The prosthetic valve according to any one of previous embodiments, wherein the two layers in the fabric have a different lateral width.

The prosthetic valve according to any one of previous embodiments, wherein the two layers in the fabric have a different length in longitudinal direction, preferably sections in the layer forming leaflets are larger than corresponding sections in the layer forming supporting elements.

The prosthetic valve according to any one of previous embodiments, wherein the single piece of two-layer woven fabric is made by cutting a continuous fabric into pieces of desired length, preferably with stabilized cut edges.

The prosthetic valve according to any one of previous embodiments, wherein the fabric has a plain, twill or basket weave pattern.

The prosthetic valve according to any one of previous embodiments, wherein the fabric has locally different weave pattern or weave density.

The prosthetic valve according to any one of previous embodiments, wherein the fabric contains layers with single layer thickness of about 20-200 μm, preferably layer thickness is at most 180, 150, 140, 130, 120, 110 or 100 μm and at least 30, 40, 50 or 60 μm, for example between 40 to 150 μm, or having a thickness of between 50 to 100 μm.

The prosthetic valve according to any one of previous embodiments, wherein warp and fill threads comprise at least 80 or 90 mass % or consist essentially of one type of monofilament or multifilament yarn.

The prosthetic valve according to any one of previous embodiments, wherein the warp and fill threads have a linear density of less than 120 dtex, preferably of less than 100, 80, 60, 50, 40, 30, 20 or even 15 dtex, and preferably of at least 5, 7, or 10 dtex; for example a linear density of between 5 and 30 dtex, or between 7 and 15 dtex.

The prosthetic valve according to any one of previous embodiments, wherein the warp and fill threads comprise or are made from high-performance polymeric yarn, preferably multifilament yarn having tensile strength or tenacity of at least 1 GPa The prosthetic valve according to any one of previous embodiments, wherein the warp and fill threads comprise ultra-high molecular weight polyethylene (UHMWPE) yarn.

The prosthetic valve according to previous embodiment, wherein the UHMWPE yarn is a gel-spun UHMWPE multifilament yarn having a Young's modulus of at least 30 GPa or 50 GPa, a tenacity of at least 1 or 2 GPa, and preferably an elongation at break of about 2 to 4%.

The prosthetic valve according to previous embodiments, wherein the UHMWPE yarn comprises at least 80 or 90 mass % of UHMWPE filaments, or consists essentially of UHMWPE filaments.

The prosthetic valve according to any one of previous embodiments, wherein the free margin of a leaflet has an excess length, relative to the minimum length needed for closing the valve, of at least 7%, preferably of at least 10 or 15%, and of at most 40 or 30%.

The prosthetic valve according to any one of previous embodiments, wherein the prosthetic valve comprises a leaflet that, even without pulsatile load on the valve, can form a coaptation height of more than 0.1 mm along the length of the free margin, preferably the coaptation height is at least 2, 3, 4 or 5 mm and at most 15, 13, 11, 10, 9, 8, or 7 mm, for example between 3 and 10 mm, preferably between 5 and 7 mm.

The prosthetic valve according to any one of previous embodiments, wherein the prosthetic valve further comprises a stent to which the leaflet assembly is attached, preferably the stent is a self-expandable stent.

The invention claimed is:

1. A method of making a prosthetic valve that can take a first form wherein the valve is open and a second form wherein the valve is closed, the valve comprising a leaflet assembly having at least one leaflet attached to a supporting element, the leaflet having a free margin that can move between a first position wherein the valve takes the first form and a second position wherein the valve takes the second form, the method comprising:
  (i) providing a textile structure having woven warp and fill threads forming a two-layer double weave fabric having two stacked and interconnected layers and crossing threads between the two layers, wherein the two layers have selvedges at one longitudinal edge and a continuous connection at an opposite edge to the one longitudinal edge, and wherein the two-layer woven fabric includes further connections between the two layers which create different sections that pre-define one or more leaflets in a layer; and
  (ii) forming the leaflet assembly from the textile structure by connecting two lateral edges of a single piece of the fabric to make a substantially tubular structure such that an inner layer forms the leaflet and an outer layer forms the supporting element and such that a selvedge of the textile structure forms the free margin of the leaflet.

2. The method according to claim 1, wherein the prosthetic valve has two or three leaflets.

3. The method according to claim 1, wherein the fabric has a different number of warp threads in each of the two layers to thereby define different lateral widths of the two layers.

4. The method according to claim 1, wherein one layer of the two layers in the fabric has a locally increased increasing the number of fill threads to thereby establish a different length of the one layer relative to another of the two layers.

5. The method according to claim 1, wherein the single piece of fabric is made in a continuous weaving operation as a continuous fabric that is cut into pieces of desired length, and optionally cut edges are stabilized.

6. The method according to claim 1, wherein the fabric contains layers with single layer thickness of 20-200 μm.

7. The method according to claim 1, wherein the warp and fill threads have a linear density of less than 120 dtex.

8. The method according to claim 1, wherein the warp and fill threads have a linear density of between 5 and 30 dtex.

9. The method according to claim 1, wherein the warp and fill threads comprise ultra-high molecular weight polyethylene (UHMWPE) yarn.

10. The method according to claim 1, wherein the prosthetic valve has three leaflets, and wherein the free margin of the leaflets has an excess length, relative to a minimum length needed for closing the valve, of at least 7%.

11. The method according to claim 1, further comprising attaching the leaflet assembly to a stent.

12. A method of making a leaflet assembly for a prosthetic valve as described in claim 1.

* * * * *